United States Patent [19]

Meyer

[11] 3,947,410

[45] Mar. 30, 1976

[54] BIS-OXADIAZOLE COMPOUNDS

[75] Inventor: Hans-Rudolf Meyer, Binningen, Switzerland

[73] Assignee: Ciba-Geigy Corporation, Ardsley, N.Y.

[22] Filed: Oct. 17, 1973

[21] Appl. No.: 407,117

[30] Foreign Application Priority Data

Oct. 18, 1972 Switzerland...................... 15245/72
Oct. 18, 1972 Switzerland...................... 15246/72

[52] U.S. Cl.. 260/240 D; 252/301.2 W; 260/240 R; 260/240.1; 260/307 G; 260/240 CA; 260/240.9
[51] Int. Cl.² ...................................... C07D 413/10
[58] Field of Search......... 260/240 D, 240 R, 240.1, 260/240.9, 307 G, 240 CA

[56] References Cited
UNITED STATES PATENTS

| | | | |
|---|---|---|---|
| 2,765,304 | 10/1956 | Siegrist et al. | 260/307 G |
| 3,274,184 | 9/1956 | Thompson et al. | 260/240 D |
| 3,481,949 | 12/1969 | Lynch et al. | 260/307 G |
| 3,600,383 | 8/1971 | Atkinson | 260/240 D |
| 3,644,345 | 2/1972 | Siegrist et al. | 260/240 D |
| 3,830,848 | 8/1974 | Siegrist | 260/240 CA |

FOREIGN PATENTS OR APPLICATIONS 1,506,629  12/1967  France

Primary Examiner—Arthur P. Demers
Attorney, Agent, or Firm—Joseph G. Kolodny; Edward McC. Roberts; Prabodh I. Almaula

[57] ABSTRACT

The present invention provides new bis-oxadiazole compounds of the formula

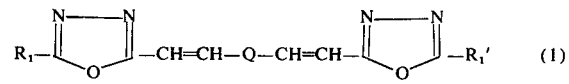

wherein $R_1$ and $R_1'$ independently of one another represent hydrogen, an optionally non-chromophorically substituted aliphatic, cycloaliphatic or araliphatic radical with up to 18 carbon atoms or an optionally non-chromophorically substituted, at most binuclear, carbocyclic or heterocyclic aromatic radical and Q represents a radical

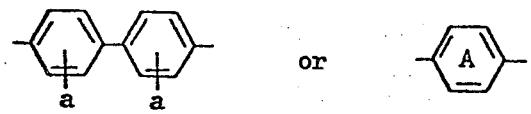

wherein $a$ represents hydrogen, halogen, alkyl with 1 to 4 carbon atoms, alkoxy with 1 to 4 carbon atoms, sulpho groups or their salts or an optionally substituted sulphamoyl group or both radicals $a$ together with the diphenylene radical represent a 9,10-dihydrophenanthrene ring and the benzene ring A can optionally be substituted by halogen, alkyl with 1 to 4 carbon atoms, sulpho groups or their salts or an optionally substituted sulphamoyl group or can possess a fused-on six-membered ring.

The new compounds are useful optical brighteners for high-molecular organic materials.

6 Claims, No Drawings

NEW BIS-OXADIAZOLE COMPOUNDS

The present invention relates to new bis-oxadiazole compounds, processes for the manufacture of these compounds and their use as optical brighteners for organic materials.

The new bis-oxadiazoles according to the present invention are compounds of the formula (1)

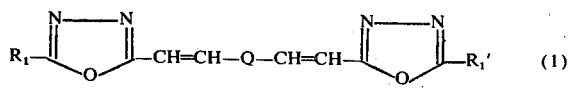 (1)

wherein $R_1$ and $R_1'$ independently of one another represent hydrogen, an optionally non-chromophorically substituted aliphatic, cycloaliphatic or araliphatic radical with up to 18 carbon atoms or an optionally non-chromophorically substituted, at most binuclear, carbocyclic or heterocyclic aromatic radical and Q represents a radical

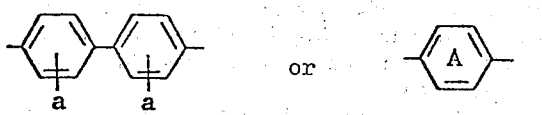

wherein $a$ represents hydrogen, halogen, alkyl with 1 to 4 carbon atoms, alkoxy with 1 to 4 carbon atoms, sulpho groups or their salts or an optionally substituted sulphamoyl group or both radicals $a$ together with the diphenylene radical represent a 9,10-dihydrophenanthrene ring and the benzene ring A can optionally be substituted by halogen, alkyl with 1 to 4 carbon atoms, sulpho groups or their salts or an optionally substituted sulphamoyl group or can possess a fused-on six-membered ring.

Possible aliphatic radicals $R_1$ and $R_2'$ are either saturated or unsaturated acyclic hydrocarbon radicals which are optionally bonded via an oxygen atom or interrupted by oxygen atoms or hetero-groups, possible cycloaliphatic radicals are predominantly optionally methyl-substituted cycloalkyl radicals with 5 or 6 ring members, and possible araliphatic radicals are aralykl and aralkenyl radicals, preferably styryl radicals. Examples of such substituents $R_1$ and $R_1'$ which may be mentioned are methyl, ethyl, n-propyl, isopropyl, n-butyl, isobutyl, sec.butyl, isobutyl, tert.butyl, methoxyethyl, acetoxyethyl, n-pentyl, sec.pentyl, isopentyl, neopentyl, 1-ethyl-propyl, vinyl, allyl methallyl, crotyl, chloromethyl, chloroethyl, cyclohexyl, cyclopentyl, benzyl, piperonyl, phenylethyl, 2-, 3- or 4-chlorobenzyl and 2-, 3- or 4-methylbenzyl. If $R_1$ and $R_1'$ denote carbocyclic aromatic radicals, they are, for example, radicals of the naphthalene series or especially radicals of the benzene series such as phenyl and diphenylyl. Possible hetero-aromatic radicals are above all pyridine, quinoline, furyl and thienyl radicals. All these radicals $R_1$ and $R_1'$ can be non-chromophorically substituted.

Non-chromophoric substituents can be either monovalent or divalent radicals, and the latter as a rule form a carbocyclic or heterocyclic ring fused onto a benzene ring. An optionally substituted sulphamoyl group is to be understood as an unsubstituted, monosubstituted and disubstituted sulphonic acid amide group of which the possible substituents are alkyl radicals with 1 to 6 carbon atoms or phenyl groups or can, with the nitrogen atom connecting them, form a heterocyclic structure which can contain yet further hetero-atoms. Such heterocyclic structures can be, for example, optionally methyl-substituted piperidino, morpholino, pyrrolidino or piperazino.

The sulphonic acid groups present in the form of salts are mostly their alkali metal, alkaline earth metal, ammonium or amine salts. The sodium salts and potassium salts are preferred.

Examples of compounds which lie within the compass of the formula (1) are the bis-oxadiazole compounds of the formula (2)

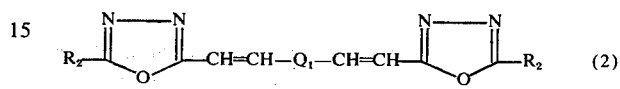 (2)

wherein $R_2$ denotes hydrogen, alkyl with 1 to 6 carbon atoms, which can have halogen, nitrile or alkoxy with 1 to 4 carbon atoms or phenoxy as substituents, alkenyl with 2 to 4 carbon atoms, cyclohexyl which is optionally substituted by methyl groups, alkoxy with 1 to 4 carbon atoms, phenylalkyl with 1 to 3 carbon atoms in the alkyl part, which is optionally substituted in the benzene nucleus by halogen, alkyl with 1 to 4 carbon atoms, alkoxy with 1 to 4 carbon atoms, methylenedioxy or phenoxy, or optionally non-chromophorically substituted phenyl, phenoxy, styryl, diphenylyl, naphthyl, pyridyl, quinolyl, thienyl-2 or furyl-2 and $Q_1$ denotes a radical

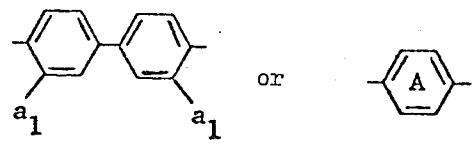

wherein $a_1$ has the meaning indicated for $a$ under the formula (1) and the remarks made with regard to the benzene ring under formula (1) apply here also.

Compounds to be particularly singled out are those of the formula (3)

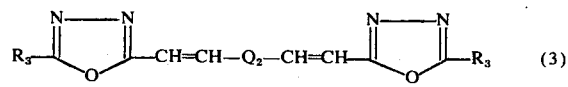 (3)

wherein $R_3$ denotes styryl, phenyl, diphenylyl, naphthyl, pyridyl, quinolyl, thienyl-2, 5-phenyl-thienyl-2, furyl-2 or phenyl substituted by halogen, such as fluorine, chlorine or bromine, alkyl with 1 to 5 carbon atoms, cycloalkyl with 5 or 6 carbon atoms, alkoxy with 1 to 4 carbon atoms, phenoxy, carboxyl or its salts, carbalkoxy with 2 to 9 carbon atoms, nitrile, methylenedioxy, sulpho groups or their salts, carbamoyl or sulphamoyl optionally substituted at the nitrogen by alkyl with 1 to 6 carbon atoms or phenyl, alkylsulphonyl or alkoxysulphonyl with 1 to 6 carbon atoms, phenylsulphonyl or phenoxysulphonyl optionally substituted by halogen or alkyl with 1 to 4 carbon atoms, amino, alkanoylamino with 2 to 4 carbon atoms or alkanoyloxy with 2 to 4 carbon atoms and $Q_2$ denotes a radical

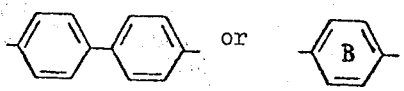

wherein the benzene ring B can optionally be substituted by halogen, alkoxy with 1 to 4 carbon atoms, a sulpho group or its salts, or sulphamoyl optionally substituted at the nitrogen by alkyl with 1 to 6 carbon atoms or phenyl.

Compounds to be mentioned especially are those of the formula (4)

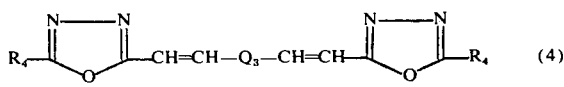

wherein $R_4$ denotes alkyl with 1 to 4 carbon atoms, diphenylyl, naphthyl, pyridyl, quinolyl, thienyl-2, 5-phenyl-thienyl-2 or a radical

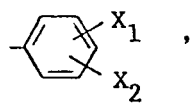

wherein $X_1$ represents hydrogen, halogen, alkyl with 1 to 4 carbon atoms, alkoxy with 1 to 4 carbon atoms, carbalkoxy with 2 to 5 carbon atoms or the sulpho group or its salts and $X_2$ represents hydrogen, halogen, alkyl with 1 to 4 carbon atoms or alkoxy with 1 to 4 carbon atoms or $X_1$ and $X_2$ together represent methylenedioxy and $Q_3$ denotes a radical

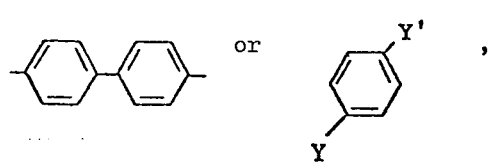

wherein Y and Y' independently of one another represent hydrogen, halogen or the sulpho group or its salts.

Compounds of particular practical interest are those of the formula (1) which have a symmetrical structure and correspond to the formula (5)

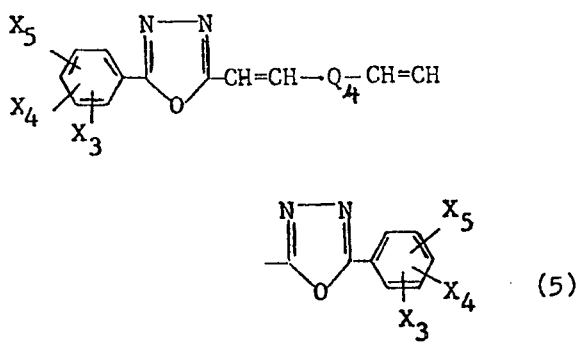

wherein $X_3$ denotes hydrogen, halogen, especially chlorine or bromine, alkyl with 1 to 5 carbon atoms, alkoxy with 1 to 4 carbon atoms, phenyl, phenoxy, carboxyl or its salts, carbalkoxy with 2 to 5 carbon atoms, nitrile, sulpho groups or their salts, $X_4$ and $X_5$ independently of one another denote hydrogen, chlorine, alkyl with 1 to 5 carbon atoms or alkoxy with 1 to 4 carbon atoms or two of the X-symbols $X_3$, $X_4$ and $X_5$ denote methylenedioxy and $Q_4$ denotes a radical

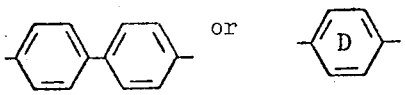

wherein the benzene ring D can optionally be substituted by chlorine, alkoxy with 1 to 4 carbon atoms or the sulpho group or its salts, and, in particular, compounds of the formula (6)

(6) 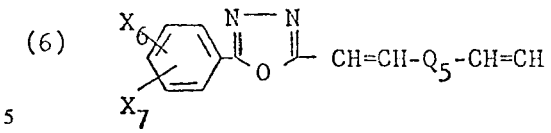

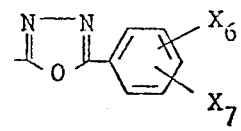

wherein $X_6$ denotes hydrogen, chlorine, alkyl with 1 to 4 carbon atoms, alkoxy with 1 to 4 carbon atoms or phenyl, $X_7$ denotes hydrogen, chlorine or alkyl with 1 to 4 carbon atoms and $Q_5$ denotes 4,4'-diphenylylene or 1,4-phenylene.

Amongst the compounds of the formula (6), the bis-oxadiazole compounds of the formulae (7) and (8) shown below (7) 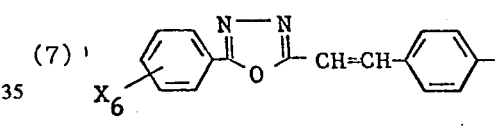

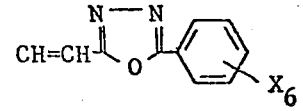

(8) 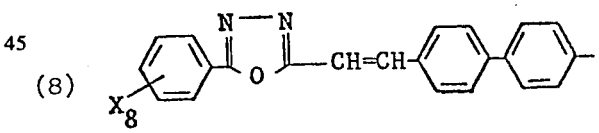

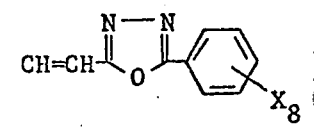

are preferred, in which $X_6$ denotes hydrogen, chlorine, alkyl with 1 to 4 carbon atoms, alkoxy with 1 to 4 carbon atoms or phenyl and $X_8$ denotes hydrogen, chlorine, alkyl with 1 to 4 carbon atoms or alkoxy with 1 to 4 carbon atoms.

As regards the formulae (2) to (8) it should be noted generally that — unless further details are stated — halogen is preferably chlorine and alkyl is to be understood as either straight-chain or branched alkyl. In the case of the carbamoyl or sulphamoyl group substituted at the nitrogen by alkyl with 1 to 6 carbon atoms — as provided, for example, under the formula (3) — the alkyl substituents of the carbamoyl or sulphamoyl group can also form, with the corresponding nitrogen atom, a hetero-ring which can contain further hetero-atoms and can optionally be substituted by alkyl groups with 1 to 4 carbon atoms. Morpholino, piperidino, piperazino and N-methylpiperazino may here be mentioned as examples of such hetero-rings. Examples of possible salts of carboxyl and sulpho groups are the alkali metal, alkaline earth metal, ammonium and amine salts. In this case, again, the sodium salts and potassium salts are preferred.

The bis-oxadiazole compounds of the formula (1) or of the subordinate formulae can be manufactured analogously to processes which are in themselves known. An advantageous procedure to follow is to react, simultaneously or successively, one mol of a compound of the formula (9)

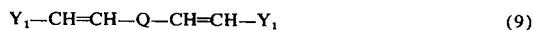

$Y_1-CH=CH-Q-CH=CH-Y_1$ (9)

with one mol each of the compounds of the formulae (10) and (11)

$R_1-Y_2$ (10)

and

$R_1'-Y_2$ (11)

wherein $R_1$, $R_1'$ and Q have the abovementioned meaning and one of the symbols $Y_1$ and $Y_2$ denotes a carboxyl group or a functionally modified carboxyl group and the other denotes a hydrazide group, to give a diacylhydrazine compound of the formula (12)

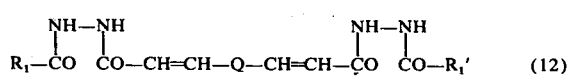

$$\underset{R_1-CO}{\overset{NH-NH}{|}} \underset{CO-CH=CH-Q-CH=CH-CO}{} \underset{CO-R_1'}{\overset{NH-NH}{|}} \quad (12)$$

and subjecting this compound to cyclisation to give the bis-oxadiazole compound. Functionally modified carboxyl groups can be, for example, carboxylic acid halides, such as chlorides and bromides, carboxylic acid amide, carboxylic acid alkyl esters with 2 to 5 carbon atoms and nitrile groups. Carboxylic acid chlorides are preferred.

The reaction between the particular components of the formulae (9) and (10) or (11) can be carried out with or without isolation of the initially produced intermediate stage of the formula (12) by heating to temperatures above 100°C, appropriately to 120° – 300°C, advantageously in the presence of an inert organic solvent such as toluene, xylenes, chlorobenzene, dichlorobenzenes, trichlorobenzene or nitrobenzene or, if acid chlorides are used, preferably in the presence of a catalytically active or acid-binding agent, for example in pyridine bases, such as picolines or pyridine, or further tertiary amines such as triethylamine. The conversion into the oxdiazolyl compound is as a rule effected by treating the diacylhydrazine compound of the formula (12) with agents which split off water, such as phosphorus oxychloride, phosphorus trichloride, phosphorus pentachloride, phosphorus pentoxide, polyphosphoric acid, sulphuric acid, sulphuryl chloride, oleum-dimethylformamide, zinc chloride, aluminium chloride or p-toluenesulphonic acid or, preferably, thionyl chloride, at temperatures between 100° and 250°C. If desired, high-boiling organic solvents such as, for example, dimethylformamide, dichlorobenzene, trichlorobenzene, nitrobenzene, pyridine and aliphatic, optionally etherified, hydroxy compounds, for example propylene glycol, ethylene glycol monoethyl ether, diethylene glycol diethyl ether or diethylene glycol dibutyl ether, can also be used conjointly.

A particularly advantageous embodiment for the manufacture of compounds of the formula (2) consists, for example, of first reacting a dicarboxylic acid dihalide of the formula (13)

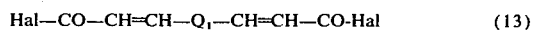

Hal—CO—CH=CH—$Q_1$—CH=CH—CO-Hal (13)

with 2 mols of a hydrazide of the formula (14)

$R_2$—CONHNH$_2$ (14)

preferably in the presence of a catalytically active agent or agent which binds hydrogen halide, and subjecting the resulting acylhydrazine compound to an oxadiazole cyclisation reaction by treatment with agents which split off water, for example thionyl chloride at between 120° and 200°C. In the above formulae, Hal denotes chlorine or bromine, whilst $Q_1$ and $R_2$ have the meaning indicated earlier.

Another manufacturing process for compounds of the formula (1) which is advantageous in many cases consists of simultaneously or successively reacting one mol of a compound of the formula (15)

$Z_1 - Q - Z_1$ (15)

with one mol of a compound of the formula (16)

(16)

and one mol of a compound of the formula (17)

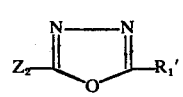

(17)

if appropriate with subsequent saponification and decarboxylation of the carboxylic acid derivatives first produced in the condensation; in these formulae, the remarks made earlier apply to Q, $R_1$ and $R_1'$, and of $Z_1$ and $Z_2$ one denotes a HOC group and the other denotes methyl, the —CH$_2$COOH grouping or its functional acid derivatives or one of the groupings of the formulae

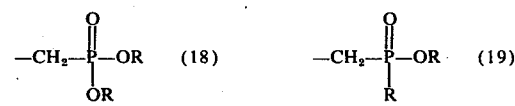

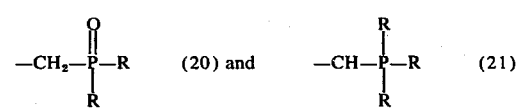

wherein R represents alkyl with 1 to 5 carbon atoms or phenyl. Possible functional derivatives of the HOOC—CH$_2$— group are here, for example, —CH$_2$CN, —CH$_2$CONH$_2$, CH$_2$COCl or —CH$_2$COOR', wherein R' denotes an alkyl radical with 1 to 4 carbon atoms.

The modification of possible carboxyl groups in the substituents $R_1$ and $R_1'$ is effected, after having formed the bis-oxadiazole compound according to the above manufacturing process, by converting compounds according to the formula (1) or subordinate formulae, possessing free carboxyl groups or their salts, into corresponding acid halides and manufacturing the corresponding esters or amides from these according to methods which are in themselves known.

In accordance with the reaction principle explained above it is possible, for example, to react dialdehydes of the formula (22)

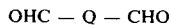

$$\text{OHC} - Q - \text{CHO} \qquad (22)$$

with monofunctional compounds of the formulae

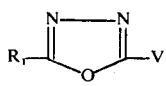 (23) or 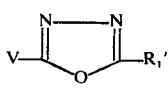 (24)

or to react monoaldehydes of the formulae

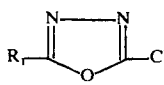 (25) or 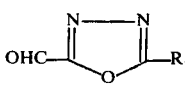 (26)

with bifunctional compounds of the formula (27)

$$V - Q - V \qquad (27)$$

wherein V denotes methyl, the —$CH_2COOH$ grouping or its functional acid derivatives or one of the phosphorus-containing substituents of the formulae (18), (19), (20) or (21) and Q, $R_1$ and $R_1'$ have the meaning indicated under the formulae (15), (16) and (17).

A possible preferred method of manufacture for producing compounds according to the formula (2) is the process variant, amongst those mentioned above, according to which one mol of a compound of the formula (28)

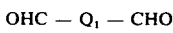

$$\text{OHC} - Q_1 - \text{CHO} \qquad (28)$$

is reacted with two mols of a compound of the formula (29)

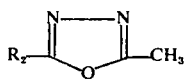 (29)

wherein $Q_1$ and $R_2$ have the meaning indicated under the formula (2).

The condensation of a compound of the formula (15) with the compounds of the formulae (16) and (17) can be carried out in the melt, preferably in an inert solvent, at temperatures between 20° and 150°C, if necessary in the presence of a catalyst. Examples of possible solvents are hydrocarbons, such as toluene and xylene, or alcohols such as methanol, ethanol, isopropanol, butanol, glycol, glycol ethers such as 2-methoxyethanol, hexanols, cyclohexanol and cyclooctanol, and also ethers, such as diisopropyl ether, tetrahydrofuran and dioxane. Polar organic solvents such as dimethylformamide, N-methylpyrrolidone and dimethylsulphoxide are particularly suitable. Some of the reactions can also be carried out in aqueous solution. Examples of suitable catalysts are tertiary amines such as pyridine, picoline, triethylamine piperidine, zinc chloride, boric acid, boric anhydride, acetic anhydride, p-toluenesulphonic acid and alkali metal acetates, alkali metal hydroxides or alkaline earth metal hydroxides, alkali metal alcoholates, phthalimide-potassium and potassium carbonate.

The new compounds defined above display a more or less pronounced fluorescences fluorescence the dissolved or finely divided state. They can be used for the optical brightening of the most diverse synthetic, semi-synthetic or natural organic materials or substances which contain such organic materials.

The following groups of organic materials, where optical brightening hereof is relevant, may be mentioned as examples of the above, without the survey given below being intended to express any restriction thereto I. Synthetic organic high molecular materials:

a. Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on α,β-unsaturated carboxylic acids or derivatives of such carboxylic acids, especially on acrylic compounds (such as, for example, acrylic esters, acrylic acid, acrylonitrile, acrylamides and their derivatives or their methacryl analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example, polyamides of the polycaprolactam type and also polymers which are obtainable both via polyaddition and via polycondensation, such as polyethers or polyacetals.

c. Polycondensation proucts or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols such as, for example alkyd resins) polyesters, polyamides (for example hexamethylenediamine adipate), maleate resins, malamine resins, their precondensates and analogues, polycarbonates and silicones, d. Polyaddition products such as polyurethanes (cross-linked and non-crosslinked) and epoxide resins.

II. Semi-synthetic organic materials, for examples, cellulose esters of varying degrees of esterification (so-called 2½ acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, foils, lacquers, coatings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions dispersions, latices, pastes or waxes.

Fibre materials can, for example, be in the form of endless filaments (stretched or unstretched), staple fibres, flocks, hanks, textile filaments, yarns, threads, fibre fleeces, felts, waddings, flocked structures or woven textile fabrics, textile laminates, knitted fabrics and paper, cardboards or paper compositions.

The compounds to be used according to the invention are of importance, inter alia, for the treatment of organic textile materials, especially woven textile fabrics. Where fibres, which can be in the form of staple fibres or endless filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at a temperatures of about 20° to 140°C, for example at the boiling point of the bath or near it (about 90°C). Solutions or emulsions in organic solvents can also be used for the finishing according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

addition to the starting substances (for example monomers) or intermediates (for example precondensates or prepolymers), that is to say before or during the polymerisation, polycondensation or polyaddition, powdering onto polymer chips or granules for spinning compositions, bath dyeing of polymer chips or granules for spinning compositions, metered addition to spinning melts or spinning solutions, and Application to the tow before stretching.

The new optical brighteners according to the present invention can, for example, also be employed in the following use forms:

Mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints.

b. Mixed with so-called "carriers," wetting agents, plasticisers, swelling agents, anti-oxidants, light protection agents, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear", "Permanent-press" or "no-iron"), as well as flameproof finishes, soft handle finishes, anti-soiling finishes or antti-static finishes, or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches."

f. As additives to the most diverse industrial products in order to render these more marketable (for example improving the appearance of soaps, detergents, pigments), g. In combination with other optically brightening substances, h. In spinning bath preparations, that is to say as additives to spinning baths such as are used for improving the slip for the further processing of synthetic fibres, or from a special bath before the stretching of the fibre.

i. As scintillators for various purposes of a photographic nature, such as, for example, for electrophotographic reproduction or supersensitisation, and for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of the brighteners at temperatures below 75°C, for example at room temperature, and to subject them to a dry heat treatment at temperatures above 100°C, it being generally advisable additionally to dry the fibre material beforehand at a moderately elevated temperature, for example at not less than 60°C and up to about 130°C. The heat treatment in the dry state is then advantageously carried out at temperatures between 120° and 255°C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 per cent by weight. However, amounts of up to about 0.8 per cent by weight and optionally of up to about 2 per cent by eight can be employed. For most practical purposes, amounts between 0.0005 and 0.5 per cent by weight are of preferred interest.

The new optical brightening agents — insofar as they contain groups which confer solubility in water — are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, synthetics, soluble salts or sulphonic acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerinesulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The washing agents can further contain for example: antistatic agents, skin protection agents which restore fat, such as lanolin, enzymes, antimicrobial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of cellulose fibres, polyamide fibres, cellulose fibers with a high quality finish, polyester fibres, wool and the like.

The washing treatment is carried out as follows, for example:

The textiles indicated are treated for 1 to 30 minutes at 20° to 100°C in a wash liquor which contains 1 to 10 g/kg of a built-up composite washing agent and 0.05 to 1%, relative to the weight of the washing agent, of the claimed brightening agents. The liquor ratio can be 1:3 to 1:50. After washing, the textiles are rinsed and dried in the usual manner. The wash liquor can contain 0.2 g/l of active chlorine (for example as hypochlorite) or 0.1 to 2 g/l of sodium perborate as a bleaching additive.

In the examples the parts, unless otherwise stated, are always parts by weight and the percentages are always percentages by weight. Unless otherwise noted melting points and boiling points are uncorrected.

EXAMPLE 1

A mixture of 10.5 g of biphenyl-4,4'-dialdehyde, 12.0 g of malonic acid, 0.1 ml of piperidine and 30 ml of pyridine is stirred for 2 hours at 45°–50°C and 3 hours at 100°C. After cooling, 50 ml of water and 30 ml of concentrated hydrochloric acid are added to the suspension and the mixture is filtered. The residue is repeatedly washed with water, dried and extracted by boiling with 50 ml of dioxane, and 13.2 g of the dicarboxylic acid of the formula (30)

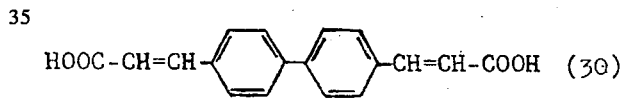

are obtained as a sparingly soluble pale yellow powder of melting point 330°C.

Analysis: (After high vacuum sublimation at approx. 300°C): $C_{18}H_{14}O_4$ (294.29): Calculated: C 73, 46%; H 4.80%; Found: C 73.73%; H 4.74%

A mixture of 14.7 g of dicarboxylic acid of the formula (30), 21.8 g of phosphorus pentachloride and 50 ml of chlorobenzene is heated under reflux for one-fourth hour, in the course of which complete solution occurs. The product which crystallises out on cooling is filtered off and dried in vacuo at 70°C. 8.0 g of the acid chloride of the formula (31)

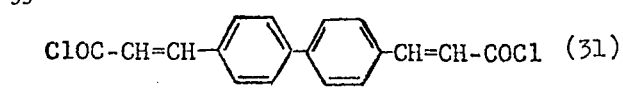

are obtained in the form of light yellow crystals of melting point 239°C.

4.8 g of the dicarboxylic acid dichloride of the formula (31) and 41. g of benzhydrazide are stirred in 90 ml of anhydrous dichlorobenzene and 0.1 ml of pyridine for 1 hour under reflux. 6.5 ml of thionyl chloride are added dropwise at the boil, over the course of one-fourth hour, to the resulting suspension of the dihydrazide of the formula (32)

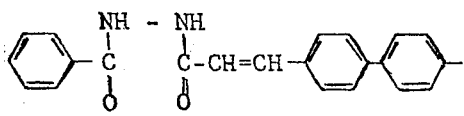
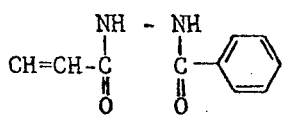

(32)

after which the dihydrazide dissolves. After completion of the evolution of hydrogen chloride, the mixture is cooled and the product which has precipitated is filtered off, repeatedly washed with ethanol and dried. 3.7 g of the compound of the formula (33)

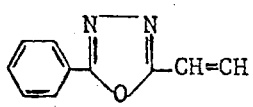
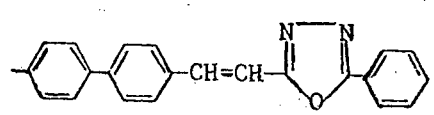

(33)

are obtained, the compound being in the form of light yellow crystals of melting point 271°C after recrystallisation from dodecylbenzene and dimethylformamide.

If instead of benzhydrazide m-toluic acid hydrazide is used, the compound of the formula (34)

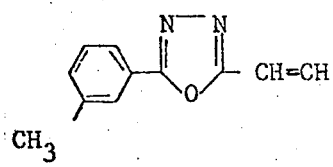
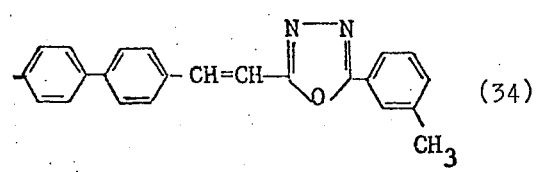

(34)

is obtained, melting point 271°C (after recrystallisation from dodecylbenzene and dimethylformamide).

The compounds of the general formula (35)

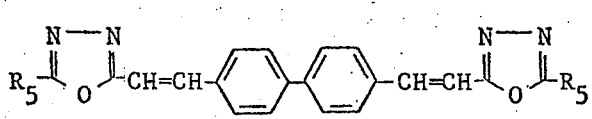

listed in the Table I which follows are obtained in a similar manner.

Table I

| Formula No. | $R_5$ | Melting point |
|---|---|---|
| (36) | 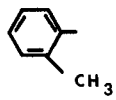 CH$_3$ | 259° |
| (37) | 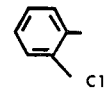 Cl | 225° |
| (38) | 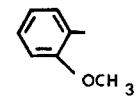 OCH$_3$ | 233° |
| (39) |  Cl | 296° |

EXAMPLE 2

12.7 g of powdered potassium hydroxide (88% strength) are introduced in portions, with vigorous stirring into a solution of 12.8 g of 2-methyl-5-phenyl-1,3,4-oxadiazole and 8.4 g of biphenyl-4,4'-dialdehyde in 100 ml of dimethylformamide. The mixture is stirred for 16 hours at 50°–55°C, during which time it assumes a dark colouration. After cooling to room temperature, 25 ml of water are added to the reaction mixture and the precipitated is filtered off and washed with 10 ml of dimethylformamide and repeatedly with methanol and water. The dried residue (15.3 g) is recrystallised from 220 ml of dimethylformamide with the aid of active charcoal and fuller's earth. 9.1 g of the compound of the formula (33) are obtained in the form of pale yellow crystals of melting point 274°C.

If instead of potassium hydroxide the equivalent amount of potassium tert.-butylate is used and an analogous procedure is followed, the compound of the formula (33) is again obtained. Instead of dimethylformamide, the condensation can also be carried out in dimethylsulphoxide or N-methylpyrrolidone.

EXAMPLE 3

Bis-oxadiazole compounds of the formula (40)

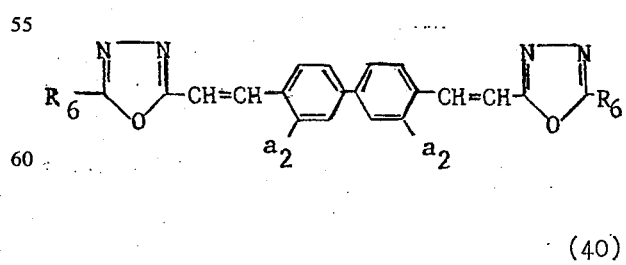

(40)

wherein $R_5$ and $a_2$ have the meaning indicated in Table II below, are manufactured in a similar manner to that described in Example 1 or 2.

Table II

| Formula No. | R₆ | a₂ |
|---|---|---|
| (41) | 4-CH₃-C₆H₄- | H |
| (42) | 4-Cl-C₆H₄- | H |
| (43) | 4-CH₃O-C₆H₄- | H |
| (44) | 3-OCH₃-C₆H₄- | H |
| (45) | 4-(CH₃)₃C-C₆H₄- | H |
| (46) | C₆H₅- | CH₃ |
| (47) | C₆H₅- | OCH₃ |
| (48) | C₆H₅- | Cl |
| (49) | 3,4-Cl₂-C₆H₃- | H |
| (50) | 3,4-Cl₂-C₆H₃- | H |
| (51) | 3-Cl-4-CH₃-C₆H₃- | H |
| (52) | 2-Br-C₆H₄- | H |
| (53) | 2-OCOCH₃-C₆H₄- | H |
| (54) | 4-biphenylyl- | H |
| (55) | 3,4-methylenedioxyphenyl- | H |
| (56) | 2-pyridyl- | H |
| (57) | 2-OCH₂CH₃-C₆H₄- | H |
| (58) | 2,3-(CH₃)₂-C₆H₃- | H |
| (59) | 2,4-(CH₃)₂-C₆H₃- | H |
| (60) | 2,5-(CH₃)₂-C₆H₃- | H |

EXAMPLE 4

A mixture of 23.5 g of dicarboxylic acid of the formula (30), 33.3 g of phosphorus pentachloride and 70 ml of perchloroethylene is heated for 30 minutes at the reflux temperature and the solvent is then stripped off in vacuo. The resulting acid chloride of the formula (31) is stirred with 19.1 g of nicotinic acid hydrazide in 200 ml of anhydrous pyridine for 1 hour at the reflux temperature and the suspension is filtered at room temperature. After washing the residue with pyridine and water and subsequent drying, 8.5 g of dihydrazide of melting point 291°C (decomposition) are obtained.

This dihydrazide is stirred in 40 ml of o-dichlorobenzene, 8 ml of pyridine and 4.5 ml of phosphorus oxychloride for 30 minutes at the reflux temperature, in the course of which it dissolves. The solution is cooled, 20 ml of methanol are added, and the precipitate is filtered off, repeatedly washed with methanol and dried. 7.6 g of the dioxadiazole of the formula

(61) 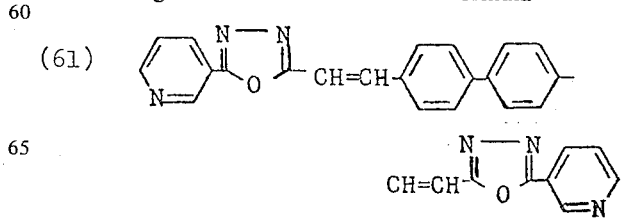

are obtained, melting at 313°C after recrystallisation from dodecylbenzene and dichlorobenzene.

EXAMPLE 5

10.9 g of benzhydrazide and 10.2 g of p-phenylenediacrylic acid dichloride [P. Ruggli and W. Theilheimer, Helv. Chim. Acta 24 (1941) 899–918] in 100 ml of anhydrous pyridine are stirred for one quarter hour at 50°C and one half hour at the reflux temperature. The resulting suspension is cooled and filtered. The residue is washed with ethanol and dried. 12.1 g of the dihydrazide of the formula (62)

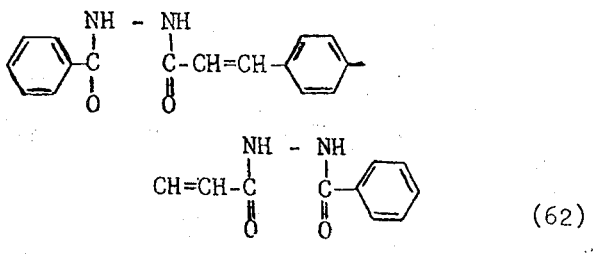

of melting point 325°C (after recrystallisation of a sample from diethylene glycol) are obtained.

11.0 g of the crude dihydrazide of the formula (62) in 50 ml of o-dichlorobenzene and 0.1 ml of pyridine are stirred under reflux whilst adding 5.3 ml of thionyl chloride dropwise. The dihydrazide gradually dissolves. After the evolution of hydrogen chloride has ceased, the solution is cooled. The product which has crystallised off is filtered off, washed with dimethylformamide and dried. 7.3 g of the dioxadiazole of the formula (63)

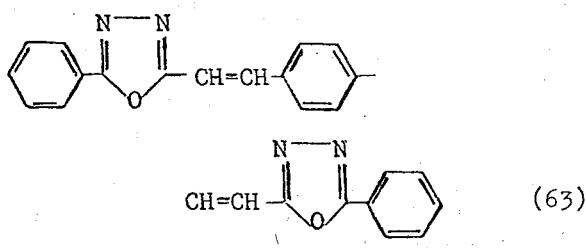

of melting point 276°C (after recrystallisation from dimethylformamide and o-dichlorobenzene, with the aid of aluminium oxide for decolourisation) are obtained.

EXAMPLE 6

A solution of 9.8 g of 2-chloromethyl-5-phenyl-1,3,4-oxadiazole (Belgian Patent No. 773,033) and 20 mg of zinc chloride in 26.2 g of triethyl phosphite is slowly heated to the reflux temperature and kept for 1 hour at 170°–180°C. After the elimination of ethyl chloride has ceased, the excess triethyl phosphite is evaporated off in vacuo and the residue is cooled to room temperature.

The resinous residue, which contains the phosphonate of the formula (64)

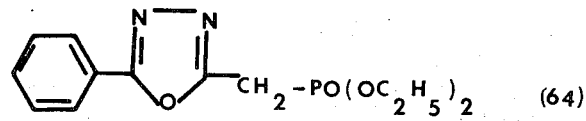

together with 2.7 g of terephthalaldehyde are dissolved in 50 ml of dimethylformamide and 4.3 g of sodium methylate are introduced in small portions over the course of one quarter hour, whilst stirring. The reaction mixture is stirred for a further 3 hours at 45°–50°C, cooled and mixed with 40 ml of water. The product which has crystallised out is filtered off, repeatedly washed with methanol and water and dried. 2.7 g of a yellow compound of the formula (63), which melts at 276°C after recrystallisation from dimethylformamide, are obtained.

EXAMPLE 7

15.9 g of powdered potassium hydroxide (88% strength) are introduced into a solution of 16.0 g of 2-methyl-5-phenyl-1,3,4-oxadiazole and 6.7 g of terephthalaldehyde in 100 ml of dimethylformamide, whilst stirring vigorously. The mixture is stirred for 16 hours at 50°–55°C, during which it assumes a dark colour. After cooling to room temperature, 20 ml of water and 5 ml of glacial acetic acid are added to the reaction mixture. The resulting precipitate is filtered off and repeatedly washed with methanol and water. The dried residue (6.8 g) is then boiled up in 30 ml of dimethylformamide, the suspension is cooled and filtered and the residue is washed with dimethylformamide. 5.6 g of the compound of the formula (63) are obtained in the form of pale greenish-yellow crystals of melting point 276°C.

If instead of potassium hydroxide 28.0 g of potassium tert.-butylate are used, and an analogous procedure is followed, 5.6 g of the compound of the formula (63) are again obtained.

Instead of dimethylformamide, the condensation can also be carried out in dimethylsulphoxide or N-methylpyrrolidone.

EXAMPLE 8

A mixture of 17.0 g of p-phenyl-benzhydrazide, 10.2 g of p-phenylene-diacrylic acid dichloride, 0.2 ml of pyridine and 200 ml of anhydrous trichlorobenzene is slowly heated to the boil whilst stirring and is kept under reflux for 1 hour. After adding 0.2 ml of pyridine, 8.8 ml of thionyl chloride are added dropwise over the course of one hour, in the course of which the intermediate product which has precipitated redissolves.

After the evolution of hydrogen chloride has ceased, the solution is cooled and the product obtained is filtered off. It is washed with dimethylformamide and ethanol and dried. 18.3 g of the compound of the formula (65)

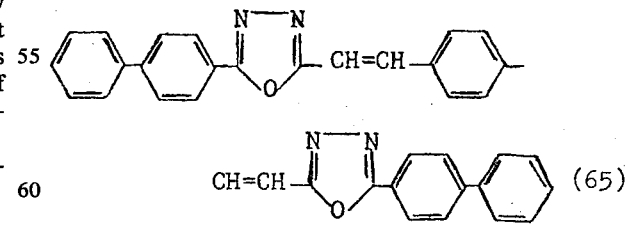

are obtained, melting at 331°C after recrystallisation from N-methylpyrrolidone and trichlorobenzene.

The compounds of the general formula (66)

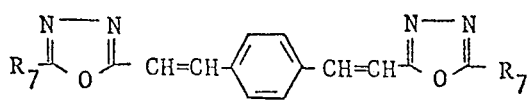

listed in Table III are obtained in a similar manner but using o-dichlorobenzene instead of trichlorobenzene.

Table III

| Formula No. | R₇ | Melting point |
|---|---|---|
| (67) | CH₃–⟨⟩– | 304° |
| (68) | ⟨⟩– (CH₃) | 210° |
| (69) | ⟨⟩– (CH₃) | 247° |
| (70) | Cl–⟨⟩– | 340° |
| (71) | ⟨⟩– (Cl) | 228° |
| (72) | ⟨⟩– (Cl) | 287° |
| (73) | CH₃O–⟨⟩– | 280° |
| (74) | ⟨⟩– (OCH₃) | 193° |
| (75) | (CH₃)₃C–⟨⟩– | 340° |
| (76) | CH₃— | 252° |
| (77) | ⟨⟩–⟨S⟩– | 311° |

EXAMPLE 9

A solution of 1.34 g of terephthalaldehyde and 4.64 g of the oxadiazole of the formula (78)

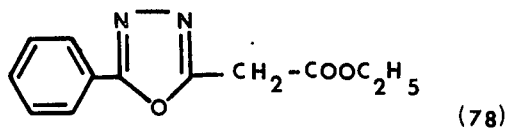

(78)

(Ann.Chim. 2 (1967) 169–181) in 100 ml of toluene and 0.2 ml of piperidine is boiled for 23 hours under reflux whilst azeotropically distilling the water formed.

The reaction product is completely concentrated by evaporation in vacuo and the residue is recrystallised from 20 ml of ethylene glycol monomethyl ether. 1.6 g of the compound of the formula (79)

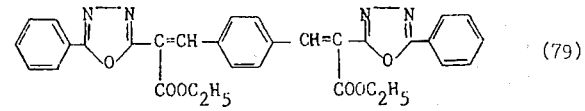

(79)

are obtained. Light yellow, felted small needles of melting point 176°C are obtained after recrystallisation from perchloroethylene and n-butanol.

2.4 g of the compound of the formula (79) are stirred with 1.2 g of potassium tert.-butylate in 50 ml of absolute ethanol for 2 hours at the reflux temperature. The reaction product is evaporated in vacuo, the residue is boiled up in 10 ml of water and after cooling to room temperature 3 ml of concentrated hydrochloric acid are added. The resulting free dicarboxylic acid is filtered off, washed with water until neutral, dried in vacuo and heated for 2 hours to 230°C whilst excluding atmospheric oxygen. The residue is taken up in boiling dimethylformamide and the solution is clarified by filtering it while hot and is allowed to cool. The product which has precipitated is filtered off, washed with dimethylformamide and dried in vacuo at 100°C. The compound of the formula (63), of melting point 269°–276°C, is obtained.

EXAMPLE 10

25.5 g of p-phenylene-diacrylic acid dichloride are introduced over the course of half an hour into a solution of 80.0 g of hydrazine hydrate and 200 ml of ethanol, whilst stirring and cooling, in such a way that the temperature does not rise above 40°C. The mixture is then heated to 70°C for 1 hour and for one quarter hour to the refluxing temperature. After cooling to room temperature, the reaction mixture is filtered and the residue is washed with methanol and dried (18.5 g).

This product is stirred in 100 ml of dimethylformamide and 20 ml of pyridine at the reflux temperature. 16.3 ml of benzoyl chloride are then added dropwise to the suspension over the course of 10 minutes. After a further 2 hours the mixture is cooled, 30 ml of water are added, the whole is filtered and the residue is washed with methanol and dried (16.0 g).

This product is stirred in 80 ml of o-dichlorobenzene under reflux after having adding 0.15 ml of pyridine, and 12.6 ml of thionyl chloride are introduced dropwise. After the evolution of hydrogen chloride has ceased, the mixture is cooled and filtered and the residue is washed with dimethylformamide and dried (8.3 g). After recrystallisation from dimethylformamide, dodecylbenzene and o-dichlorobenzene, the compound of the formula (63) of melting point 272°–276°C, is obtained.

EXAMPLE 11

6.9 g of nicotinic acid hydrazide and 6.4 g of p-phenylenediacrylic acid chloride in 100 ml of anhydrous pyridine are stirred for one hour at the reflux temperature. The suspension is cooled and filtered and the residue is washed with pyridine and water and dried. 8.6 g of the dihydrazide of the formula (80)

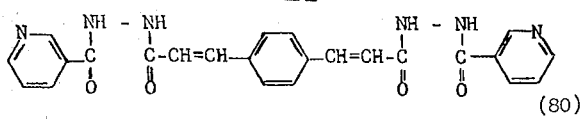

(80)

melting at approx. 325°C are obtained.

This compound is then stirred in 40 ml of o-dichlorobenzene, 8 ml of pyridine and 4.5 ml of phosphorus oxychloride for one hour at the reflux temperature. A further 10 ml of pyridine are added, the mixture is cooled and filtered and the residue is washed with methanol and dried. 5.1 g of the dioxadiazole of the formula (81)

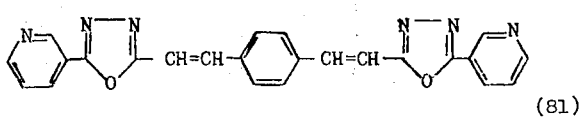

(81)

are obtained, pale yellow crystals of melting point 298°C after recrystallisation from dodecylbenzene and dimethylformamide.

EXAMPLE 12

10.4 g of terephthalic acid ethyl ester hydrazide and 6.4 g of p-phenylene-diacrylic acid dichloride in 80 ml of anhydrous pyridine are stirred for 1 hour at the reflux temperature. The resulting suspension is cooled and filtered. The residue is washed with methanol and dried, and 11.3 g of dihydrazide of melting point 332°C (decomposition) are obtained. This product is stirred in 120 ml of o-dichlorobenzene, 0.1 ml of pyridine and 4.5 ml of phosphorus oxychloride for 1 ½ hours at the reflux temperature. After the evolution of hydrogen chloride has ceased, the mixture is cooled and filtered and the residue is repeatedly washed with alcohol and dried. 9.9 g of the dioxadiazole of the formula (82)

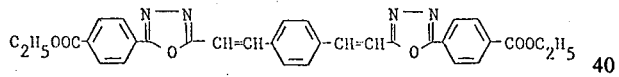

are obtained, melting point 320°C (after recrystallisation from N-methylpyrrolidone and o-dichlorobenzene).

EXAMPLE 13

Bis-oxadiazole compounds of the formula (83)

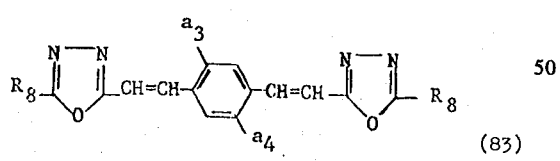

(83)

wherein $R_8$, $a_3$ and $a_4$ have the meanings indicated in Table IV below, are manufactured in a similar manner to that described in Examples 5, 7, 8 or 11.

Table IV

| Formula No. | $R_8$ | $a_3$ | $a_4$ |
|---|---|---|---|
| (84) | phenyl with $CH_3O$ | H | H |
| (85) | phenyl | Cl | Cl |
| (86) | phenyl | Cl | H |
| (87) | phenyl with Cl, Cl | H | H |
| (88) | phenyl with Cl, Cl | H | H |
| (89) | phenyl with $CH_3$, Cl | H | H |
| (90) | phenyl with Br | H | H |
| (91) | phenyl with $OCH_2CH_3$ | H | H |
| (92) | phenyl with $OCOCH_3$ | H | H |
| (93) | phenyl with $CH_3$, $OCOCH_3$ | H | H |
| (94) | phenyl with $-O-CH_2-O-$ | H | H |
| (95) | phenyl with $CH_3O$, $OCH_3$ | H | H |
| (96) | phenyl with $CH_3O$, $CH_3O$ | H | H |
| (97) | phenyl with $CH_3O$, $OCH_3$ | H | H |
| (98) | phenyl with $CH_3$, $CH_3$ | H | H |
| (99) | phenyl with $CH_3$, $CH_3$ | H | H |
| (100) | phenyl with $CH_3$, $CH_3$ | H | H |

Table IV-continued

| Formula No. | R₈ | a₃ | a₄ |
|---|---|---|---|
| (101) | 2,4-dimethylphenyl | H | H |
| (102) | 1-naphthyl | H | H |
| (103) | 2-naphthyl | H | H |
| (104) | thienyl | H | H |
| (105) | pyridyl | H | H |
| (106) | quinolinyl | H | H |

EXAMPLE 14

A solution of 2.1 g of the compound of the formula (63) in 10 ml of chlorosulphonic acid is warmed to 70°C for 30 minutes, cooled and poured out onto ice, whereupon a yellow product precipitates. This is filtered off, repeatedly washed with ice water and dried in vacuo over calcium chloride 2.6 g of the monosulphochloride of the formula (107)

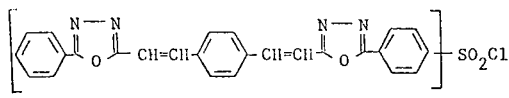

are obtained, melting point 206°C (decomposition), after recrystallisation from xylene and chlorobenzene in the presence of a little thionyl chloride.

0.5 g of this compound is dissolved in 15 ml of hot pyridine, 2 ml of water are added and the mixture is heated for 15 minutes under reflux. It is evaporated to dryness on a rotary evaporator and the residue is crystallised from 10 ml of n-butanol. 0.3 g of crude pyridinium salt of the corresponding sulphonic acid

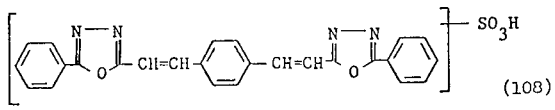

is obtained, melting point approx. 260°C (after recrystallisation from methylcellosolve-water).

EXAMPLE 15

4.7 g of the compound of the formula (63) are introduced into 25 ml of oleum (25% strength) at room temperature, whilst stirring. After 2 hours, the solution is poured onto 50 g of ice, which does not result in the precipitation of a solid product. The mixture is neutralised to pH 6–7 with crystalline sodium acetate, whilst hot, and is cooled, the salts which have precipitated are filtered off and the filtrate is evaporated to dryness on a rotary evaporator. 23.2 g of a yellow, readily water-soluble sulphonation product

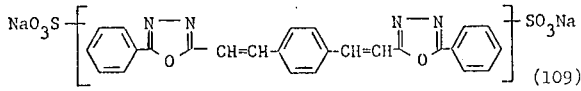

are obtained, which still contains a large amount of sodium sulphate and sodium acetate. The product can be used, without further purification, for the brightening of polyamide and cellulose.

EXAMPLE 16

A polyester fabric based on terephthalic acid/ethylene glycol (for example "Dacron") is padded at room temperature with an aqueous dispersion with contains, per liter, 2 g of the compound of the formula (27) and 1 g of an addition product of about 8 mols of ethylene oxide to 1 mol of p-tert.octylphenol, and is dried at about 100°C. The dry material is subsequently briefly subjected to a heat treatment at 220°C. The material treated in this way displays a strong brightening effect, with good fastness to light.

If instead of the compound of the formula (63) a compound of the formula (33), (34), (38), (69), (71), (72) or (81) is employed, similar results are obtained.

If instead of the polyester fabric described above, a fabric of a polyester produced by co-condensation with 2 to 5 mol% of the (sulphonate) sodium salt of isophthalic acid-5-sulphonic acid (Dacron 64) is used, the abovementioned compounds again give a strong brightening of good fastness to light.

EXAMPLE 17

100 parts of granules of a terephthalic acid/ethylene glycol polyester are intimately mixed with 0.05 part of one of the compounds of the formulae (33), (37), (39), (63), (68), (71), (72) or (75) and the mixture is fused at 285°C, whilst stirring. After spinning the spinning composition through customary spinnerets, brightened polyester fibres of good fastness to light are obtained.

EXAMPLE 18

1,000 parts of granular polyamide-6 are mixed for 12 hours in a tumbler vessel with 3 parts of titanium dioxide (rutile modification) and 1 part of one of the compounds of the formulae (33), (34), (63) or (75). The mixture is fused with exclusion of atmospheric oxygen and the melt is spun in the usual manner. The resulting filaments are strongly brightened.

EXAMPLE 19

An intimate mixture of 100 parts of polyvinyl chloride, 3 parts of stabiliser (Advastat BD 100: Ba/Cd complex), 2 parts of titanium dioxide, 59 parts of dioctyl phthalate and 0.01 to 0.2 part of one of the compounds of the formulae (33), (34), (38), (63), (68), (71), (72), (74) or (75) is milled on a calender at 150 to 155°C to give a film. The opaque polyvinyl chloride film thus obtained has a substantially higher degree of whiteness than a film which does not contain the optical brightener.

EXAMPLE 20

A casting composition of 10 g of polyacrylonitrile, 0.2 g of titanium dioxide (anatase modification) as a delustering agent and 40 ml of dimethylformamide, which contains 5 mg of one of the compounds of the formulae (33), (63), (68), (72) or (75), is poured onto a glass plate and spread by means of a metal rod to give a thin film. After drying, the film is strongly brightened.

EXAMPLE 21

A 15% strength casting composition of acetylcellulose in acetone which contains — relative to the dry weight of plastic — 2% of anatase (titanium dioxide) as delustering agent, and 0.04% of one of the compounds of the formulae (68) or (74), is poured on a glass plate and spread by means of a metal rod to give a thin film. After drying, the film shows a substantially higher degree of whiteness than a film produced in the same way which does not contain an optical brightener.

EXAMPLE 22

100 parts of polystyrene and 0.1 part of one of the compounds of the formulae (68), (72) or (75) are fused, with exclusion of air, in a tube of 1 cm diameter for 20 minutes at 210°C. After cooling, an optically brightened polystyrene composition of good fastness to light is obtained.

EXAMPLE 23

A polyester fabric is treated in an autoclave, using a liquor ratio of 1:25, in a bath of the following composition: 0.16% (relative to the fibre weight of the fabric to be brightened) of the compound (66) in a finely dispersed form, 1.0 g of an ethoxylated stearyl alcohol and 1,000 ml of softened water.

The bath is heated from 40°C to 120°C over the course of 30 minutes, left at 120°C for a further 30 minutes and cooled, and the fabric is rinsed and dried. A strongly brightened polyester fabric of good fastness to light is thus obtained.

Similar effects are also obtained with compounds of the formulae (63), (68), (74) or (81) on a fabric of a polyester which has been produced by co-condensation with 2 to 5 mol% of the (sulphonate) sodium salt of isophthalic acid-5-sulphonic acid (Dacron 64).

EXAMPLE 24

A polyamide fibre fabric (Perlon) is introduced, using a liquor ratio of 1:40, into a bath at 60°C which contains (relative to the fabric weight) 0.1% of the brightener of the formula (109) and, per liter, 1 g of 80% strength acetic acid and 0.25 g of an addition product of 30 to 35 mols of ethylene oxide to one mol of technical stearyl alcohol. The mixture is warmed to the boil over the course of 30 minutes and is kept at the boil for 30 minutes. After rinsing and drying, a strong brightening effect of excellent fastness to light is obtained. If instead of the polyamide-6 fabric a polyamide-66 (nylon) fabric is used, similarly good brightening effects are obtained.

Finally, it is also possible to carry out the treatment under HT conditions, for example for 30 minutes at 130°C. For this type of use, it is advisable to add 3 g/l of hydrosulphite to the liquor.

Similar effects are obtained with the compound of the formula (108).

EXAMPLE 25

A bleached cotton fabric is introduced, using a liquor ratio of 1:25, into a bath at 20°C which contains (relative to the fabric weight) 0.1 to 0.2% of the brightener of the formula (109). The bath is heated to 50°C over the course of 15 minutes and 5 g of crystalline sodium sulphate are then added per liter of liquor. After a further 15 minutes, the fabric is rinsed briefly and is then dried. The cotton treated in this way is whiter than the untreated fabric.

What we claim is:

1. A bis-oxadiazole corresponding to the formula (3)

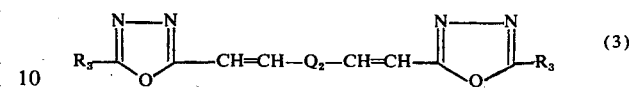

wherein $R_3$ is styryl, phenyl, diphenylyl, naphthyl, pyridyl, quinolyl, thienyl-2, furyl-2, 5-phenyl-thienyl-2 or phenyl substituted by halogen, alkyl with 1 to 5 carbon atoms, cycloalkyl with 5 or 6 carbon atoms, alkoxy with 1 to 4 carbon atoms, phenoxy, carboxyl or its salts, carbalkoxy with 2 to 9 carbon atoms, nitrile, methylenedioxy, sulpho groups or their salts, carbamoyl or sulphamoyl which is unsubstituted or substituted at the nitrogen by alkyl with 1 to 6 carbon atoms or phenyl, alkylsulphonyl or alkoxysulphonyl with 1 to 6 carbon atoms, phenylsulphonyl or phenoxysulphonyl unsubstituted or substituted by halogen or alkyl with 1 to 4 carbon atoms, amino, alkanoylamino with 2 to 4 carbon atoms or alkanoyloxy with 2 to 4 carbon atoms; and $Q_2$ is a radical

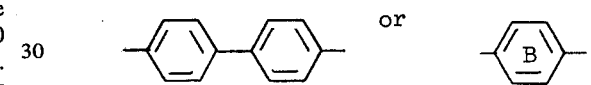

wherein the benzene ring is unsubstituted or substituted by halogen, alkoxy with 1 to 4 carbon atoms, a sulpho group or its salts, or sulphamoyl unsubstituted or substituted at the nitrogen by alkyl with 1 to 4 carbon atoms or phenyl.

2. A bis-oxadiazole according to claim 1, corresponding to the formula (4)

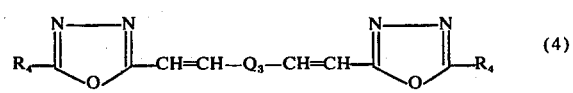

wherein $R_4$ is alkyl with 1 to 4 carbon atoms, diphenylyl, naphthyl, pyridyl, quinolyl, thienyl-2, 5-phenyl-thienyl-2 or a radical

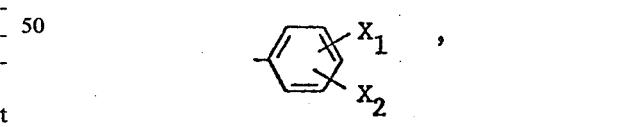

wherein $X_1$ represents hydrogen, halogen, alkyl with 1 to 4 carbon atoms, alkoxy with 1 to 4 carbon atoms, carbalkoxy with 2 to 5 carbon atoms or the sulpho group or its salts and $X_2$ represents hydrogen, halogen, alkyl with 1 to 4 carbon atoms or alkoxy with 1 to 4 carbon atoms or $X_1$ and $X_2$ together represent methylenedioxy and $Q_3$ is a radical

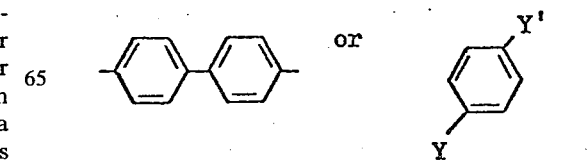

wherein Y and Y' independently of one another represent hydrogen, halogen or the sulpho group or its salts.

3. A bis-oxadiazole according to claim 1, corresponding to the formula (5)

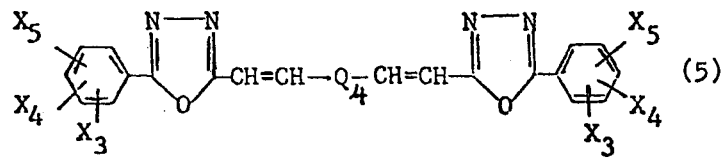

wherein $X_3$ is hydrogen, halogen, alkyl with 1 to 5 carbon atoms, alkoxy with 1 to 4 carbon atoms, phenyl, phenoxy, carboxyl or its salts, carbalkoxy with 2 to 5 carbon atoms, nitrile, sulpho groups or their salts, $X_4$ and $X_5$ independently of one another are hydrogen, chlorine, alkyl with 1 to 5 carbon atoms or alkoxy with 1 to 4 carbon atoms or two of the X-symbols $X_3$, $X_4$ and $X_5$ bound together are methylenedioxy and $Q_4$ denotes a radical

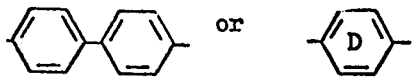

wherein the benzene ring D is unsubstituted or substituted by chlorine, alkoxy with 1 to 4 carbon atoms or the sulpho group or its salts.

4. A bis-oxadiazole according to claim 1, corresponding to the formula (6)

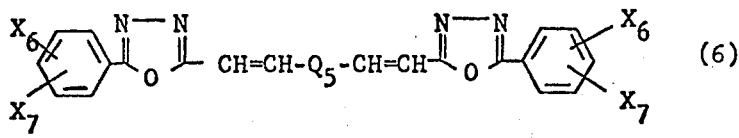

wherein $X_6$ is hydrogen, chlorine, alkyl with 1 to 4 carbon atoms, alkoxy with 1 to 4 carbon atoms or phenyl, $X_7$ is hydrogen, chlorine, or alkyl with 1 to 4 carbon atoms and $Q_5$ is 4,4'-diphenylylene or 1,4-phenylene.

5. A bis-oxadiazole according to claim 1, corresponding to the formula (7)

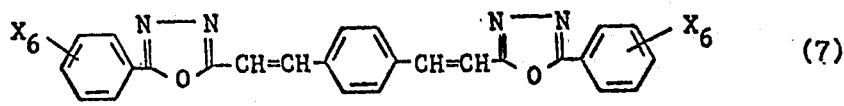

wherein $X_6$ is hydrogen, chlorine, alkyl with 1 to 4 carbon atoms, alkoxy with 1 to 4 carbon atoms or phenyl.

6. A bis-oxadiazole according to claim 1, corresponding to the formula (8)

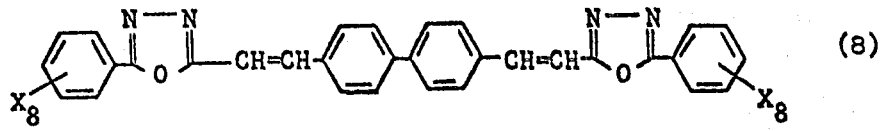

wherein $X_8$ is hydrogen, chlorine, alkyl with 1 to 4 carbon atoms or alkoxy with 1 to 4 carbon atoms.

* * * * *